(12) United States Patent
Herrmann et al.

(10) Patent No.: US 10,687,728 B2
(45) Date of Patent: Jun. 23, 2020

(54) LEARNING TECHNIQUES FOR CARDIAC ARRHYTHMIA DETECTION

(71) Applicant: Cardiac Pacemakers, Inc., St. Paul, MN (US)

(72) Inventors: Keith L. Herrmann, Minneapolis, MN (US); Sunipa Saha, Shoreview, MN (US); Arjun D. Sharma, St. Paul, MN (US); David L. Perschbacher, Coon Rapids, MN (US); Derek D. Bohn, Woodbury, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 218 days.

(21) Appl. No.: 15/840,443

(22) Filed: Dec. 13, 2017

(65) Prior Publication Data

US 2018/0177422 A1 Jun. 28, 2018

Related U.S. Application Data

(60) Provisional application No. 62/437,876, filed on Dec. 22, 2016.

(51) Int. Cl.
*A61B 5/0452* (2006.01)
*A61B 5/00* (2006.01)
(Continued)

(52) U.S. Cl.
CPC .......... *A61B 5/0452* (2013.01); *A61B 5/0022* (2013.01); *A61B 5/044* (2013.01);
(Continued)

(58) Field of Classification Search
CPC ..... A61B 5/0452; A61B 5/0428; A61B 5/044; A61B 5/7221; A61B 5/7282
(Continued)

(56) References Cited

U.S. PATENT DOCUMENTS

| 6,192,273 B1 | 2/2001 | Igel et al. |
| 8,204,581 B2 | 6/2012 | Kamousi et al. |

(Continued)

FOREIGN PATENT DOCUMENTS

| CN | 110099604 A | 8/2019 |
| WO | WO-2014169595 | 10/2014 |
| WO | WO-2016035000 A1 | 3/2016 |

OTHER PUBLICATIONS

"International Application Serial No. PCT/US2017/066050, International Preliminary Report on Patentability dated Jul. 4, 2019", 7 pgs.

(Continued)

*Primary Examiner* — Amanda K Hulbert
*Assistant Examiner* — Philip C Edwards
(74) *Attorney, Agent, or Firm* — Schwegman Lundberg & Woessner, P.A.

(57) ABSTRACT

This document discusses, among other things, systems and methods to adjust arrhythmia detection using physiological information of a patient, including detecting a candidate cardiac event about a threshold, displaying the detected candidate cardiac event to a user, receiving user information about the detected candidate cardiac event, and adjusting an arrhythmia detection threshold based upon the received user information.

20 Claims, 7 Drawing Sheets

(51) Int. Cl.
*A61B 5/044* (2006.01)
*A61B 5/0428* (2006.01)

(52) U.S. Cl.
CPC .......... *A61B 5/0428* (2013.01); *A61B 5/7221* (2013.01); *A61B 5/7282* (2013.01)

(58) Field of Classification Search
USPC ........................................................ 600/515
See application file for complete search history.

(56) References Cited

U.S. PATENT DOCUMENTS

| | | |
|---|---|---|
| 2009/0171871 A1 | 7/2009 | Zhang et al. |
| 2010/0280335 A1 | 11/2010 | Carlson |
| 2011/0263994 A1* | 10/2011 | Burns .................. A61B 5/0006 600/509 |
| 2013/0274624 A1 | 10/2013 | Mahajan et al. |
| 2014/0236029 A1 | 8/2014 | Averina et al. |
| 2016/0278659 A1 | 9/2016 | Kaib et al. |
| 2017/0039336 A1* | 2/2017 | Bitran .................. A61B 5/6801 |

OTHER PUBLICATIONS

"International Application Serial No. PCT/US2017/066050, International Search Report dated Mar. 12, 2018", 5 pgs.
"International Application Serial No. PCT/US2017/066050, Written Opinion dated Mar. 12, 2018", 5 pgs.

* cited by examiner

LEARNING TECHNIQUES FOR CARDIAC ARRHYTHMIA DETECTION

CLAIM OF PRIORITY

This application claims the benefit of priority under 35 U.S.C. § 119(e) of U.S. Provisional Patent Application Ser. No. 62/437,876, filed on Dec. 22, 2016, which is herein incorporated by reference in its entirety.

TECHNICAL FIELD

This document relates generally to medical devices, and more particularly, but not by way of limitation, to systems, devices, and methods to detect cardiac arrhythmia.

BACKGROUND

Medical devices, such as Holter devices, Insertable Cardiac Monitors (ICM), Cardiac Event Monitors (CEM), Mobile Cardiac Telemetry (MCT), and diagnostic patches can be used to monitor, detect, and in some cases, treat various cardiac conditions that can result in a reduced ability of a heart to sufficiently deliver blood to a body. In some cases, heart conditions may lead to events of rapid, irregular, or inefficient heart contractions, etc. These medical devices often use sophisticated detection techniques for detecting and treating these events.

SUMMARY

This document discusses, among other things, systems and methods of learning techniques for cardiac arrhythmia detection including adjusting cardiac arrhythmia detection using received user information of candidate cardiac events. The systems and methods disclosed herein can adjust arrhythmia detection by presenting candidate cardiac events to a user, receiving user information about the candidate cardiac events, and using the received user information to adjust parameters, thresholds, and zones to detect cardiac arrhythmias events that the user wants to see. In certain examples, the cardiac arrhythmia detection can be adjusted to identify cardiac arrhythmia events that may otherwise go undetected.

Example 1 is a system comprising: an input circuit configured to receive physiological information of a patient; an arrhythmia circuit configured to detect a candidate cardiac event about a threshold using the received physiological information of the patient; and a user interface configured to display the candidate cardiac event to a user, and to receive user information about whether the candidate cardiac event should be above or below the threshold, wherein the arrhythmia circuit is configured to adjust an arrhythmia detection threshold using the received user information that the candidate cardiac event should be above or below the threshold.

In Example 2, the subject matter of Example 1 optionally includes wherein the arrhythmia circuit is configured to detect the candidate cardiac event using a detection parameter, and wherein the arrhythmia circuit is configured to adjust at least one of the threshold or the detection parameter using the received user information that the candidate cardiac event should be above or below the threshold.

In Example 3, the subject matter of Example 2 optionally includes wherein the arrhythmia circuit is configured to detect a cardiac arrhythmia using the adjusted threshold or the adjusted detection parameter.

In Example 4, the subject matter of any one or more of Examples 1-3 optionally include wherein the arrhythmia circuit is configured to adjust the threshold within a predefined safety zone using the received user information.

In Example 5, the subject matter of Example 4 optionally includes wherein the arrhythmia circuit is configured to detect a cardiac arrhythmia using the adjusted threshold.

In Example 6, the subject matter of any one or more of Examples 1-5 optionally include wherein the arrhythmia circuit is configured to detect the candidate cardiac event within a target zone about the threshold, and wherein the target zone includes a lower boundary below the threshold, and an upper boundary above the threshold.

In Example 7, the subject matter of any one or more of Examples 1-6 optionally include wherein the received user information about whether the candidate cardiac event should be above or below the threshold includes positive received user information, neutral received user information, or negative received user information.

In Example 8, the subject matter of any one or more of Examples 2-7 optionally include a counter, wherein the arrhythmia circuit is configured to adjust a count of the counter in response to the received user information that the candidate cardiac event should be above or below the threshold, and wherein the arrhythmia circuit is configured to adjust at least one of the threshold or the detection parameter when the count exceeds an update threshold.

In Example 9, the subject matter of any one or more of Examples 1-8 optionally include wherein the arrhythmia circuit is configured to adjust a confidence parameter in response to the received user information that the candidate cardiac event should be above or below the threshold.

In Example 10, the subject matter of any one or more of Examples 6-9 optionally include wherein the threshold is centered between the upper boundary and the lower boundary.

In Example 11, the subject matter of any one or more of Examples 6-10 optionally include wherein the upper boundary is a predefined amount above the threshold and the lower boundary is a predefined amount below the threshold.

In Example 12, the subject matter of any one or more of Examples 6-11 optionally include wherein the upper boundary is a selectable amount above the threshold and the lower boundary is a selectable amount below the threshold.

Example 13 is a method comprising: receiving physiological information of a patient using an input circuit; detecting, using an arrhythmia circuit, a candidate cardiac event about a threshold using the physiological information of the patient; displaying, using a user interface, the candidate cardiac event to a user; receiving, using the user interface, user information about whether the candidate cardiac event should be above or below the threshold; and adjusting, using the arrhythmia circuit, an arrhythmia detection threshold using the received user information that the candidate cardiac event should be above or below the threshold.

In Example 14, the subject matter of Example 13 optionally includes wherein detecting the candidate cardiac event includes using a detection parameter, and wherein adjusting the arrhythmia detection threshold includes adjusting at least one of the threshold or the detection parameter using the received user information that the candidate cardiac event should be above or below the threshold.

In Example 15, the subject matter of Example 14 optionally includes detecting, using the arrhythmia circuit, a cardiac arrhythmia using the adjusted threshold or the adjusted detection parameter.

In Example 16, the subject matter of any one or more of Examples 13-15 optionally include wherein adjusting the arrhythmia detection threshold includes adjusting the threshold within a predefined safety zone using the received user information that the candidate cardiac event should be above or below the threshold.

In Example 17, the subject matter of any one or more of Examples 13-16 optionally include detecting, using the arrhythmia circuit, the candidate cardiac event within a target zone about the threshold, wherein the target zone includes a lower boundary below the threshold, and an upper boundary above the threshold.

In Example 18, the subject matter of any one or more of Examples 13-17 optionally include wherein the received user information about whether the candidate cardiac event should be above or below the threshold includes positive received user information, neutral received user information, or negative received user information.

In Example 19, the subject matter of any one or more of Examples 14-18 optionally include adjusting a count of a counter, using the arrhythmia circuit, in response to the received user information that the candidate cardiac event should be above or below the threshold; and adjusting, using the arrhythmia circuit, at least one of the threshold or the detection parameter when the count exceeds an update threshold.

In Example 20, the subject matter of any one or more of Examples 13-19 optionally include adjusting a confidence parameter in response to the received user information that the candidate cardiac event should be above or below the threshold using the arrhythmia circuit.

In Example 26, the subject matter of any one or more of Examples 1-35 to include "means for" performing any portion of any one or more of the functions or methods of Examples 1-25, or a "machine-readable medium" (e.g., non-transitory, etc.) including instructions that, when performed by a machine, cause the machine to perform any portion of any one or more of the functions or methods of Examples 1-25.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
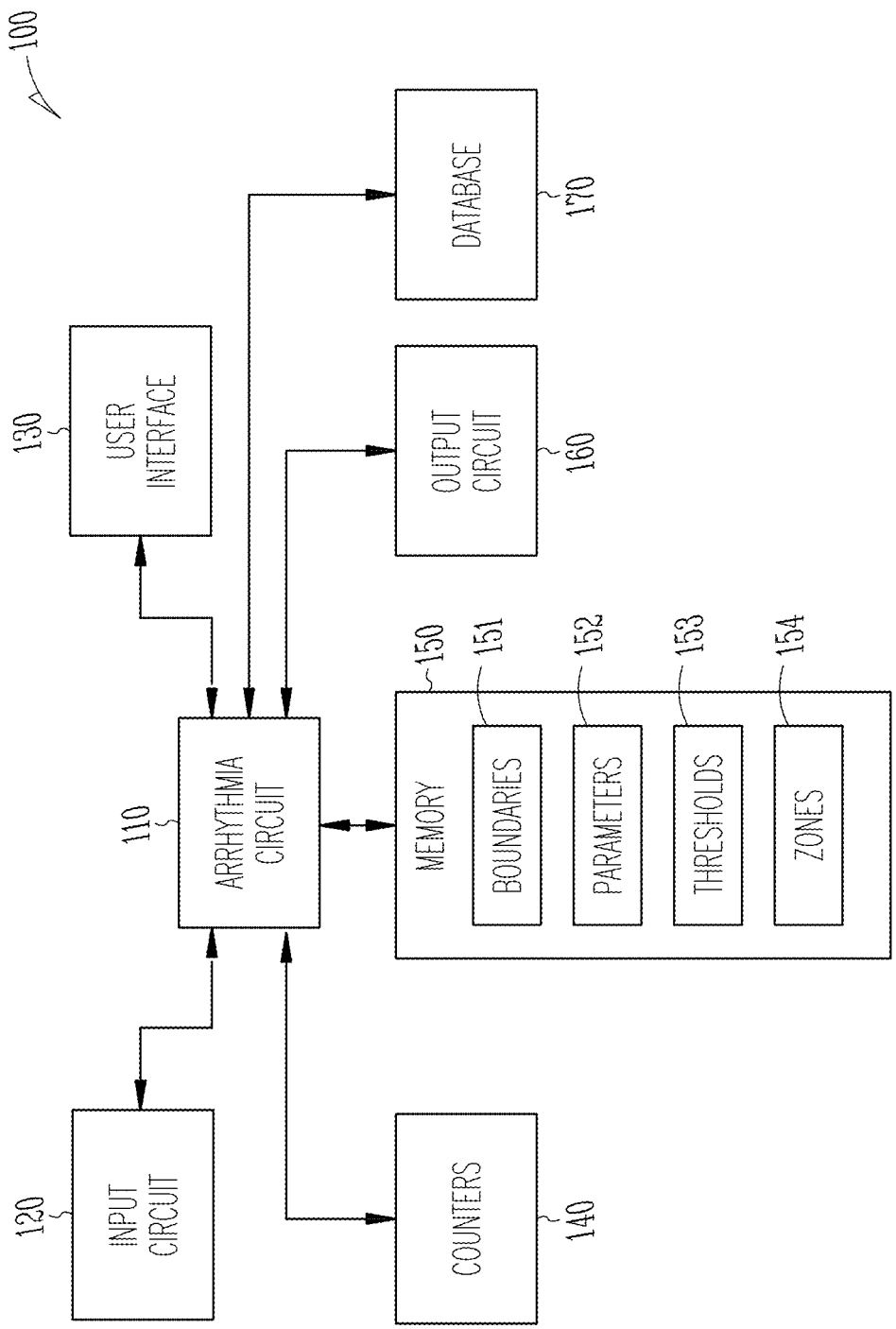
FIG. 1 illustrates an example system including an input circuit, an arrhythmia circuit, a user interface and a memory.

Cardiac monitoring devices, such as Holter devices, Insertable Cardiac Monitors (ICM), Cardiac Event Monitors (CEM), Mobile Cardiac Telemetry (MCT), and diagnostic patches, can be used to automatically detect and discriminate various cardiac events, including cardiac arrhythmias. Cardiac arrhythmias can include tachycardia, bradycardia, pauses, atrial arrhythmias, ventricular arrhythmias, or other cardiac arrhythmias. Cardiac monitoring devices can record information about one or more cardiac events, including a time of occurrence, a duration, an average heart rate, an electrocardiogram, and other information related to the cardiac events. Monitoring devices and systems can be complex and difficult to reprogram for clinicians and professionals. The number of selectable parameters, thresholds, boundaries, and zones of cardiac monitoring devices can be confusing and overwhelming to users, such as clinicians. Monitoring device data reports can also be overwhelming for clinicians, often including 50-200 pages of false positives that are unhelpful and burdensome.

The present inventors have recognized, among other things, that the complexity, confusion, and burden that existing cardiac monitoring devices present to users, including clinicians, can be significantly reduced using learning techniques for cardiac event monitoring. In certain examples, parameters, thresholds, boundaries, or zones can be adjusted based on learning techniques and user information about candidate cardiac events. Candidate cardiac events can be determined from physiological information that falls within a zone about a threshold, and presented to a user to verify that the candidate cardiac event is indeed a valid cardiac event. Learning techniques for cardiac event monitoring, as described herein, can be used to improve operation or programming of a medical device including, coupled to, or configured to receive physiological information of a patient from an input circuit.

Reduction or removal of the manual selection of parameters, thresholds, boundaries, and zones for cardiac monitoring devices can greatly simplify the user experience. Presenting the user with a single candidate cardiac event at a time and requesting positive or negative user information about the single candidate cardiac event can reduce the burden that large data dumps place on the user. Adjusting the arrhythmia detection using the received user information can lead to more accurate cardiac event detection tailored to both a specific patient's needs and the clinician's preferences. Learning techniques for cardiac event monitoring, as described herein, can improve the accuracy of cardiac event detection of a medical device including, coupled to, or configured to receive physiological information of a patient from an input circuit.

In an example, initial arrhythmia detection can be based upon a training set of real-world data. This can include initializing parameters, thresholds, boundaries, and zones used for arrhythmia detection using the training set of real-world data. An input circuit can receive physiological information of a patient (e.g., electrical or mechanical information of the heart of the patient, respiratory information of the patient, etc.). An arrhythmia circuit can be configured to detect a candidate cardiac event about a threshold using the physiological information. The user information about the candidate cardiac event can include whether the candidate cardiac event should be above or below the threshold, whether the candidate cardiac event is a reportable event, or whether the candidate cardiac event should be displayed to the user. In an example, the threshold can be associated with a parameter used for arrhythmia detection. A user interface can be configured to display the candidate cardiac event to a user and receive user information about the candidate cardiac event. In an example, the received user information consists of positive received user information, neutral received user information, and negative received user information.

In an example, the arrhythmia circuit can be configured to increment a count of a counter for positive received user information in response to positive received user information. The arrhythmia circuit can be configured to adjust arrhythmia detection when the positive count exceeds a threshold. An arrhythmia circuit can be configured to increment a count of a counter for negative received user information in response to negative received user information. The arrhythmia circuit can be configured to adjust arrhythmia detection when a negative count exceeds a threshold.

In an example, the arrhythmia circuit can be configured to adjust a confidence parameter in response to received user information. The confidence parameter can be decreased in response to negative received user information and increased in response to positive received user information. The confidence parameter can be associated with any parameter setting, threshold setting, boundary setting, or zone setting. Each parameter setting, threshold setting, boundary setting, or zone setting can have their own associated confidence parameter. In an example, the arrhythmia circuit can be configured to adjust arrhythmia detection using the confidence parameter. Arrhythmia detection can be adjusted to present more candidate cardiac events based on a parameter, threshold, boundary, or zone with a higher associated confidence parameter. In an example, adjusting the confidence parameter and arrhythmia detection using the confidence parameter can provide the user with more accurate arrhythmia notification and avoid overloading the user with false positive events. Adjusting arrhythmia detection can include adjusting an arrhythmia detection threshold.

In an example, the arrhythmia circuit can be configured to detect a candidate cardiac event within a target zone. The target zone can be situated about a threshold with a lower boundary below the threshold and an upper boundary above the threshold. Events that fall below the threshold but within the target zone can be detected as candidate cardiac events. The arrhythmia circuit can be configured to present these candidate cardiac events, one at a time, to a user and receive user information about the candidate cardiac events, one at a time.

In an example, the arrhythmia circuit can be configured to present more candidate cardiac events that fall below the threshold in response to positive received user information. The arrhythmia circuit can be configured to present fewer candidate cardiac events below the threshold in response to negative received user information. The arrhythmia circuit can be configured to present more or less of certain candidate cardiac events using a confidence parameter associated with the candidate cardiac events.

In an example, the arrhythmia circuit can be configured to adjust the lower boundary of the target zone up in response to negative received user information about the candidate cardiac events below the threshold. Detecting, displaying, receiving user information, and adjusting arrhythmia detection for candidate cardiac events within a zone, rather than just candidate cardiac events above a threshold, allows for detection of candidate cardiac events that would otherwise go undetected. Adjusting the lower boundary of the target zone in response to the received user information can increase the accuracy of arrhythmia detection, resulting in the detection of more cardiac events the user wants to see, and less of cardiac events the user does not want to see.

In certain examples, the learning techniques can be applied to a population such that the received user information from every system within the population adjusts the arrhythmia detection for all cardiac monitoring system within the population. In certain examples, the population is limited to a single clinic. In certain examples, the population includes every device within a family of devices. In certain examples, the population is a single system, or a single patient.

FIG. 1 illustrates an example system 100 including an arrhythmia circuit 110, an input circuit 120, a user interface 130, a set of counters 140, a memory 150, an output circuit 160, and a database 170. The memory 150 includes boundaries 151, parameters 152, thresholds 153, and zones 154, stored therein. In other examples, the memory 150 can be configured to store one or more other type of entry or information, or one or more other permutations or combinations of these or other entries or information. In an example, the input circuit 120 can be configured to receive physiological information from a patient, such as physiological information of a heart, or respiratory information. The input circuit 120 can be configured to receive information from a variety of physiological sensors including electrodes, a heart sound sensor, a microphone, a pressure sensor, an impedance sensor, a respiration sensor, or one or more other physiological sensors.

In an example, the arrhythmia circuit 110 can be configured to use the received physiological information to detect candidate cardiac events. The user interface 130 can be configured to present the candidate cardiac events to a user, such as a clinician, and receive user information about the candidate cardiac event from the user. The user information about the candidate cardiac event can include whether the candidate cardiac event should be above or below the threshold, whether the candidate cardiac event is a reportable event, or whether the candidate cardiac event should be displayed to the user. The arrhythmia circuit 110 can be configured to adjust arrhythmia detection using the received user information. Adjusting arrhythmia detection can include adjusting any one of the boundaries 151, the parameters 152, the thresholds 153, or the zones 154 used for arrhythmia detection.

In an example, the arrhythmia circuit 110 can be configured to use a detection parameter to detect the candidate cardiac event. The detection parameter can be a parameter from the parameters 152 stored in memory 150. The arrhythmia circuit 110 can be configured to adjust either a threshold or the detection parameter using the received user information. The threshold can be a threshold from the thresholds 153 stored in memory. The arrhythmia circuit 110 can be configured to detect a candidate cardiac event using either the adjusted threshold or adjusted detection parameter. The arrhythmia circuit 110 can be configured to adjust the threshold within a predefined safety zone using the received user information. The safety zone can be a zone from the zones 154 stored in memory 150. The arrhythmia circuit 110 can be configured to detect a candidate cardiac event using the adjusted threshold that was adjusted within the predefined safety zone.

In an example, the arrhythmia circuit 110 can be configured to detect the candidate cardiac event within a target zone about a threshold. The target zone can be a zone from the zones 154 stored in memory 150. The target zone can include a lower boundary below the threshold and an upper boundary above the threshold. The upper boundary and the lower boundary can be from the boundaries 151 stored in memory 150. The threshold can be centered between the upper and lower boundary, closer to the lower boundary, or closer to the upper boundary. In an example, the upper boundary can be a predefined amount above the threshold and the lower boundary a predefined amount below the threshold. In an example, the upper boundary can be a selectable amount above the threshold and the lower boundary a selectable amount below the threshold. In an example, the arrhythmia circuit 110 can be configured to adjust the upper boundary in response to received user input. In an example, the arrhythmia circuit 110 can be configured to adjust the lower boundary in response to received user input.

In an example, the received user information can include positive received user information, neutral received user information, or negative received user information. The arrhythmia circuit 110 can be configured to adjust a count of a counter from the set of counters 140 in response to the received user information. In an example, the counter can be a positive user information counter or a negative information counter. In an example, there can be both a positive counter and a negative counter. In an example, the arrhythmia circuit 110 can be configured to adjust at least one of the threshold or the detection parameter when the counter exceeds an update threshold. In an example, the arrhythmia circuit 110 can be configured to adjust a confidence parameter up in response to positive received user information. The arrhythmia circuit 110 can be configured to adjust a confidence parameter down in response to negative received user information.

In certain examples, the system 100 includes an output circuit 160 for providing a notification to the user or delivering arrhythmia treatments to a patient. Notifications can include alerts of arrhythmia detection adjustment, an alert that the patient needs treatment, or alerts that user information is needed in response to a candidate cardiac event. The output circuit 160 can include a speaker for providing audio notifications. The output circuit 160 can include circuitry for sending an alert to the user interface 130, a computer, a mobile phone, or other mobile computing device capable of receiving notifications.

The output circuit 160 may include circuitry for administering arrhythmia treatments including administering medication, cardioversion, or defibrillation. In certain examples, the arrhythmia circuit can be configured to treat cardiac events that exceed a confidence parameter threshold.

In certain examples, the system 100 includes a database 170. The arrhythmia circuit 110 can be configured to retrieve initialization data from the database 170. The arrhythmia circuit 110 can be configured to retrieve received user information from the database 170 for adjusting arrhythmia detection. The arrhythmia circuit 110 can be configured to record candidate cardiac event data and received user information in the database 170. In certain examples, the received user information in the database 170 is used to adjust arrhythmia detection in a population.

In certain examples, the output circuit 160 may include circuitry for communicating with the database 170 or a server. The circuitry for communicating with the database 170 may include network adapters, such as a local area network adapters, personal area network adapters, wide area network adapters, or metropolitan area network adapters. The server may include the database 170 or may communicate with the database 170 through a network connection.

Figure 2:
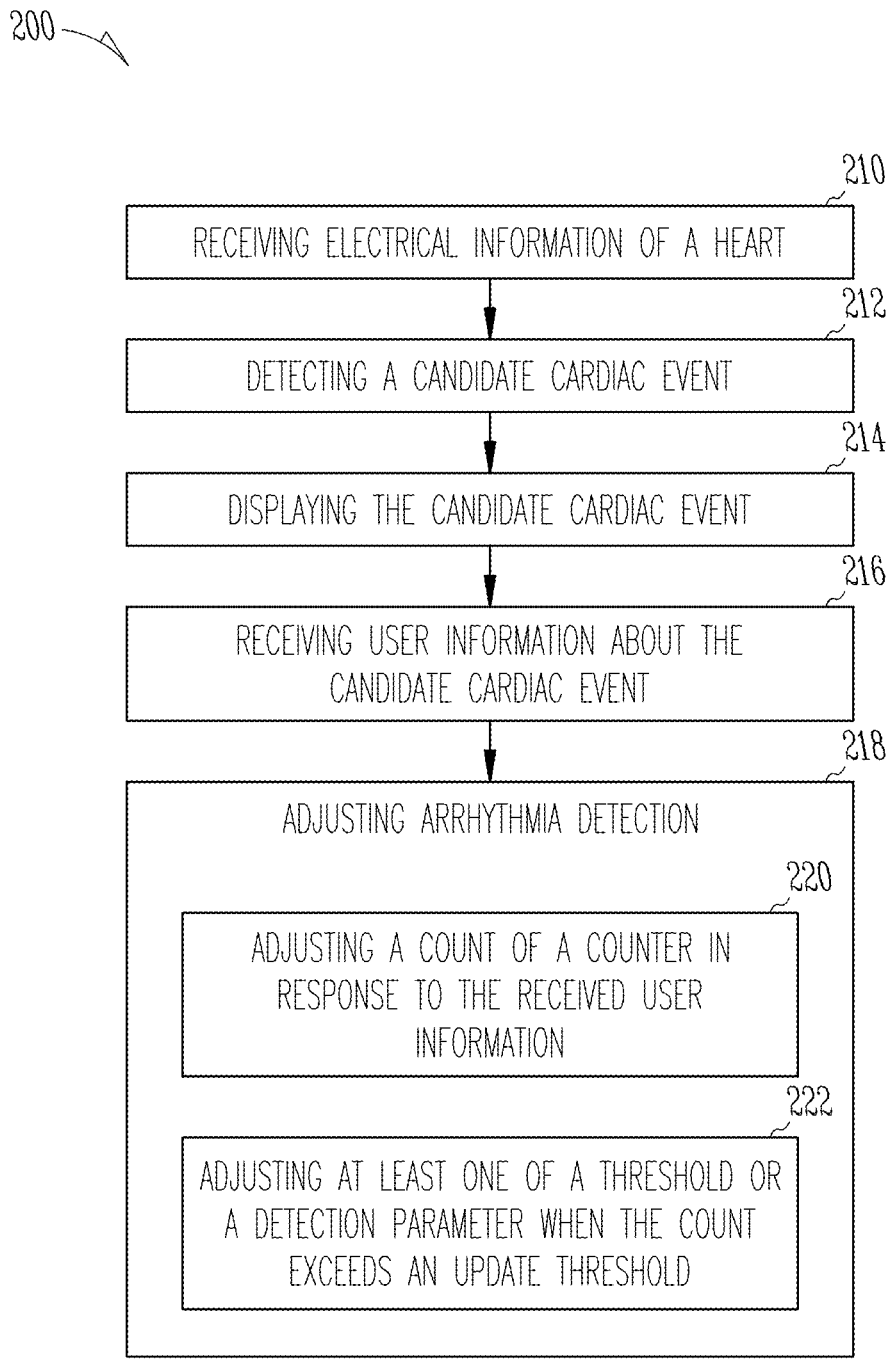
FIG. 2 illustrates an example method for detecting cardiac events from physiological information of a patient and adjusting the detection of cardiac events based upon received user information.

FIG. 2 illustrates an example method 200 for detecting cardiac events using physiological information from a patient, such as electrical or mechanical information of a heart, or respiratory information of the patient, and adjusting the detection of one or more cardiac events based upon received user information. At 210, an input circuit can receive physiological information of a patient. The input circuit can include a pressure sensor, a heart sound sensor, a set of electrodes, and an external programmer. At 212, an arrhythmia circuit can detect a candidate cardiac event. The arrhythmia circuit can use thresholds, zones, boundaries, and parameters as part of arrhythmia detection to detect the candidate cardiac event.

At 214, a user interface can display the candidate cardiac event to a user. The user interface can be a computer, a mobile compute device, an external programmer, a monitor, or other display device. At 216, the user interface can receive user information about the candidate cardiac event. The user information about the candidate cardiac event can include whether the candidate cardiac event should be above or below the threshold, whether the candidate cardiac event is a reportable event, or whether the candidate cardiac event should be displayed to the user. The user interface 216 can include a set of selectable indicators that the user can choose from to receive the user information about the candidate cardiac event. The user may be able to indicate a selection using a touch screen, computer mouse, keyboard, or other electronic user input. The received user information can be positive user information, neutral user information, or negative user information.

At 218, the arrhythmia circuit can adjust arrhythmia detection using the received user information. Adjusting arrhythmia detection can include adjusting at least one of a parameter, a threshold, a boundary, or a zone used in arrhythmia detection. In some examples, adjusting arrhythmia detection at 218 includes operations shown at 220 and 222. At 220, the arrhythmia circuit can adjust a count of a counter in response to the received user information. There may be a positive user information counter and a negative user information counter. At 222, the arrhythmia circuit can adjust at least one of the threshold or a detection parameter when the count exceeds an update threshold.

Figure 3:
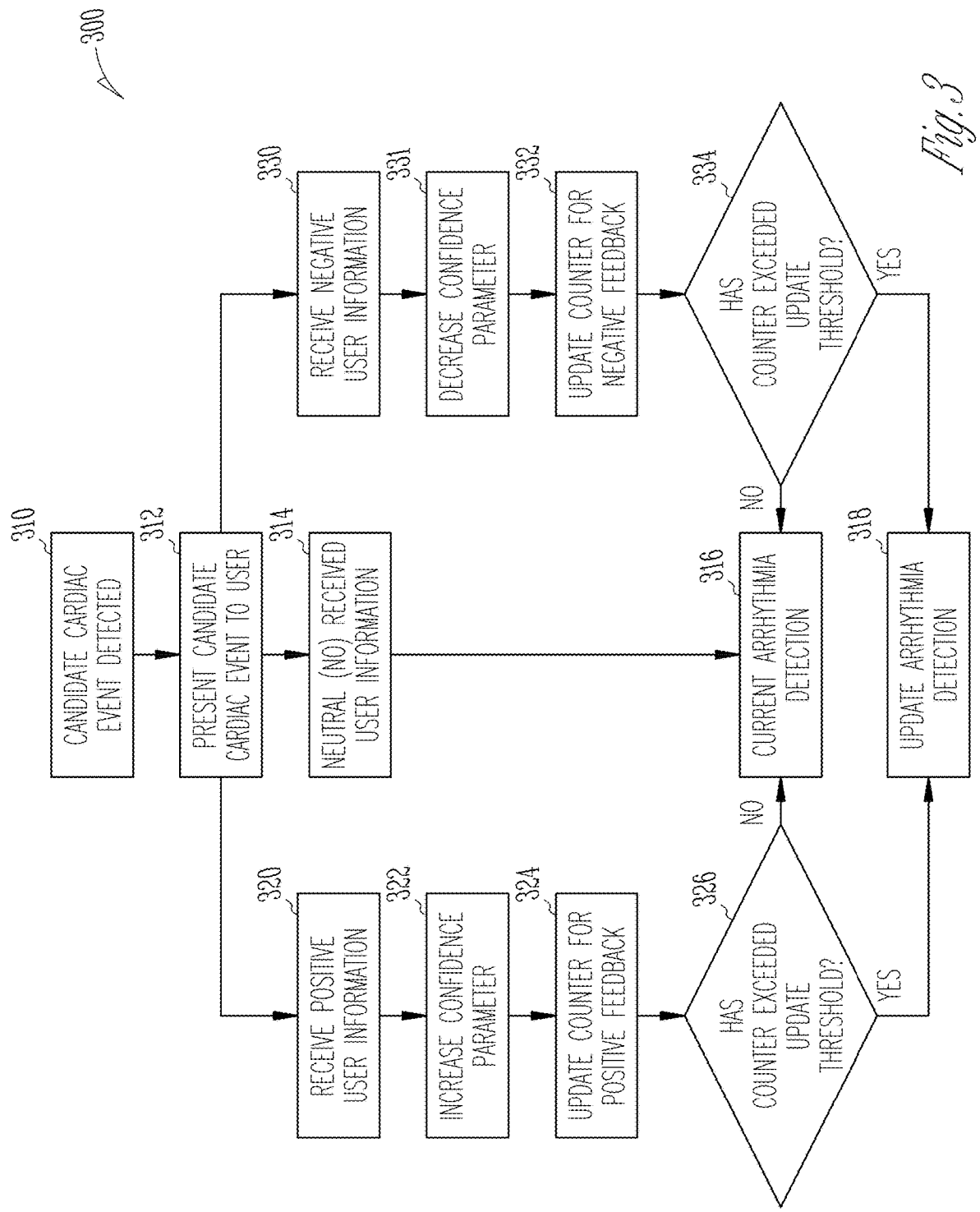
FIG. 3 illustrates an example flow chart for adjusting arrhythmia detection.

FIG. 3 illustrates an example flow chart 300 for adjusting arrhythmia detection. At 310, an arrhythmia circuit can detect a candidate cardiac event. At 312, a user interface can present the candidate cardiac event to a user. The user interface can receive user information about the candidate cardiac event from the user. The user information about the candidate cardiac event can include whether the candidate cardiac event should be above or below the threshold, whether the candidate cardiac event is a reportable event, or whether the candidate cardiac event should be displayed to the user. In an example, received user information can fit into three different categories: neutral or no received user information; positive received user information; and negative received user information.

At 314, the user interface can receive neutral user information, such as when a predetermined timeframe for user response elapses for the detected candidate cardiac event, or when the user selects a selectable indicator to move on to the next candidate cardiac event. At 316, the arrhythmia circuit can maintain a current arrhythmia detection in response to the neutral received user information.

At 320, the user interface can receive positive user information. At 322, the arrhythmia circuit can increase a confidence parameter in response to the positive received user information. At 324, the arrhythmia circuit can update a counter in response to the positive received user information. At 326, the arrhythmia circuit can determine if the updated counter exceeds an update threshold. At 318, the arrhythmia circuit can update arrhythmia detection when the updated counter exceeds the update threshold. At 316, the arrhythmia circuit can maintain the current arrhythmia detection when the updated counter does not exceed the update threshold.

At 330, the user interface can receive negative user information. At 331, the arrhythmia circuit can decrease a confidence parameter in response to negative received user information. At 332, the arrhythmia circuit can update a counter for negative received user information in response to the negative received user information. At 334, the arrhythmia circuit can determine if the updated counter exceeds an update threshold. At 318, the arrhythmia circuit can update arrhythmia detection if the updated counter exceeds the update threshold. At 316, the arrhythmia circuit can maintain the current arrhythmia detection when the updated counter does not exceed the update threshold.

Figure 4:
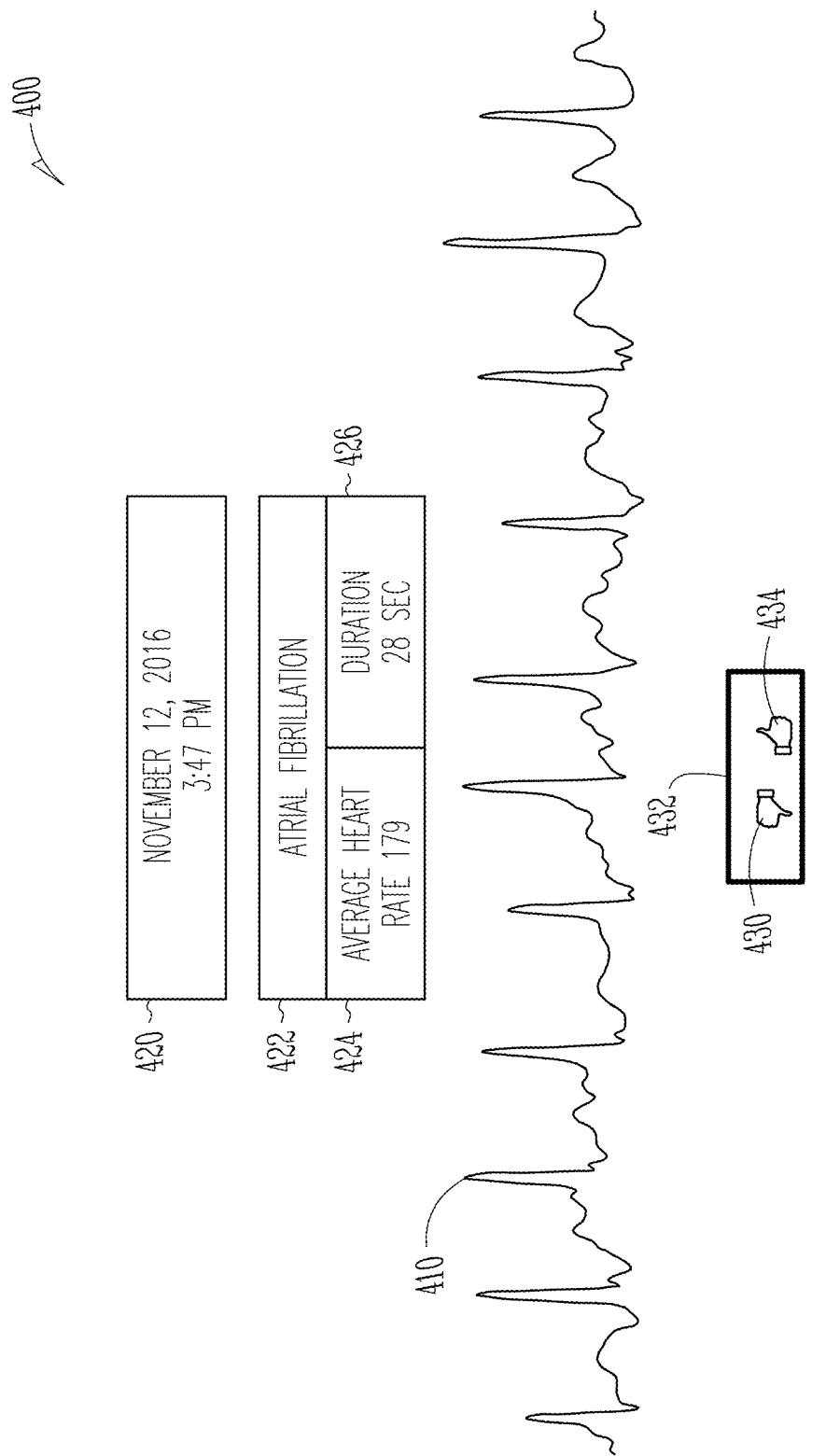
FIG. 4 illustrates an example graphical user interface for displaying a cardiac event and receiving user information.

FIG. 4 illustrates an example graphical user interface 400 for displaying a candidate cardiac event and receiving user information about the candidate cardiac event. In an example, the user interface 400 includes a date and time 420 of the candidate cardiac event, an arrhythmia type 422 of the candidate cardiac event, an average heart rate 424 during the candidate cardiac event, a duration 426 of the candidate cardiac event, an electrocardiogram 410 of the candidate cardiac event, and a user response prompt 430 for the candidate cardiac event.

The user response prompt can include a negative selectable indicator 432 and a positive selectable indicator 434. In some examples, the negative selectable indicator 432 can be a thumbs-down. In other examples, the negative selectable indicator may be an X symbol, a frowny face, or other negative indicator. In some examples, the positive selectable indicator 434 can be a thumbs-up as shown. In other examples, the positive selectable indicator may be a checkmark, a smiley face, or other positive indicator. Selection of the negative selectable indicator 432 can communicate negative user information or feedback. Selection of the positive selectable indicator 434 can communicate positive user information or feedback.

Figure 5:
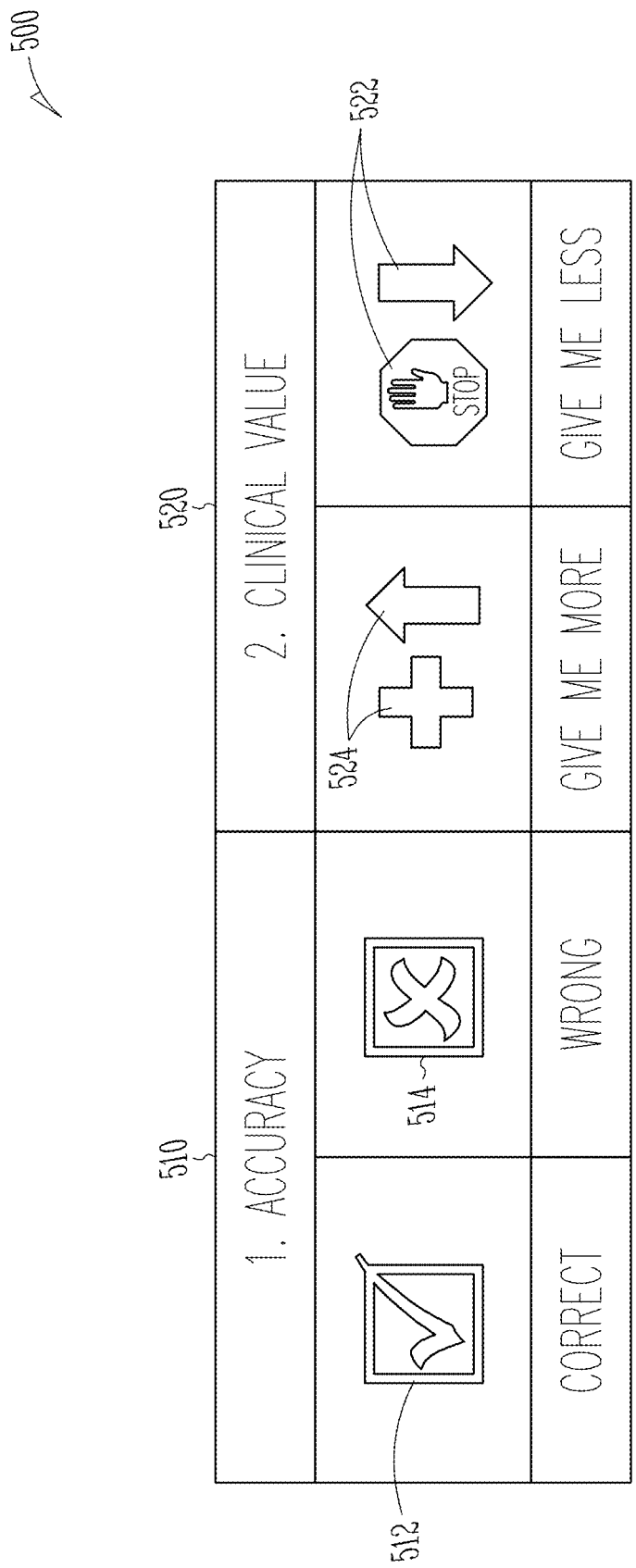
FIG. 5 illustrates an example graphical user response prompt for receiving user information.

FIG. 5 illustrates an example graphical user response prompt 500 for receiving user information. The accuracy section 510 includes a correct selectable indicator 512 and a wrong selectable indicator 514. The correct selectable indicator 512 can communicate positive user information. The wrong selectable indicator 514 can communicate negative user information. The clinical value section 520 includes a "Give Me Less" selectable indicator 522 and a "Give Me More" selectable indicator 524. Selection of the "Give Me Less" selectable indicator 522 can communicate negative user information. Selection of the "Give Me More" selectable indicator 524 can communicate positive user information.

In an example, the graphical user response prompt 500 can be the graphical user response prompt 430 of FIG. 4. In an example, a user interface can display all elements shown in the graphical user response prompt 500. In an example, the user interface can display the selectable indicators of the graphical user interface. In an example, the user interface may display only the selectable indicators from the accuracy section 510. In an example, the user interface may display only the selectable indicators from the clinical value 520 section.

Figure 6:
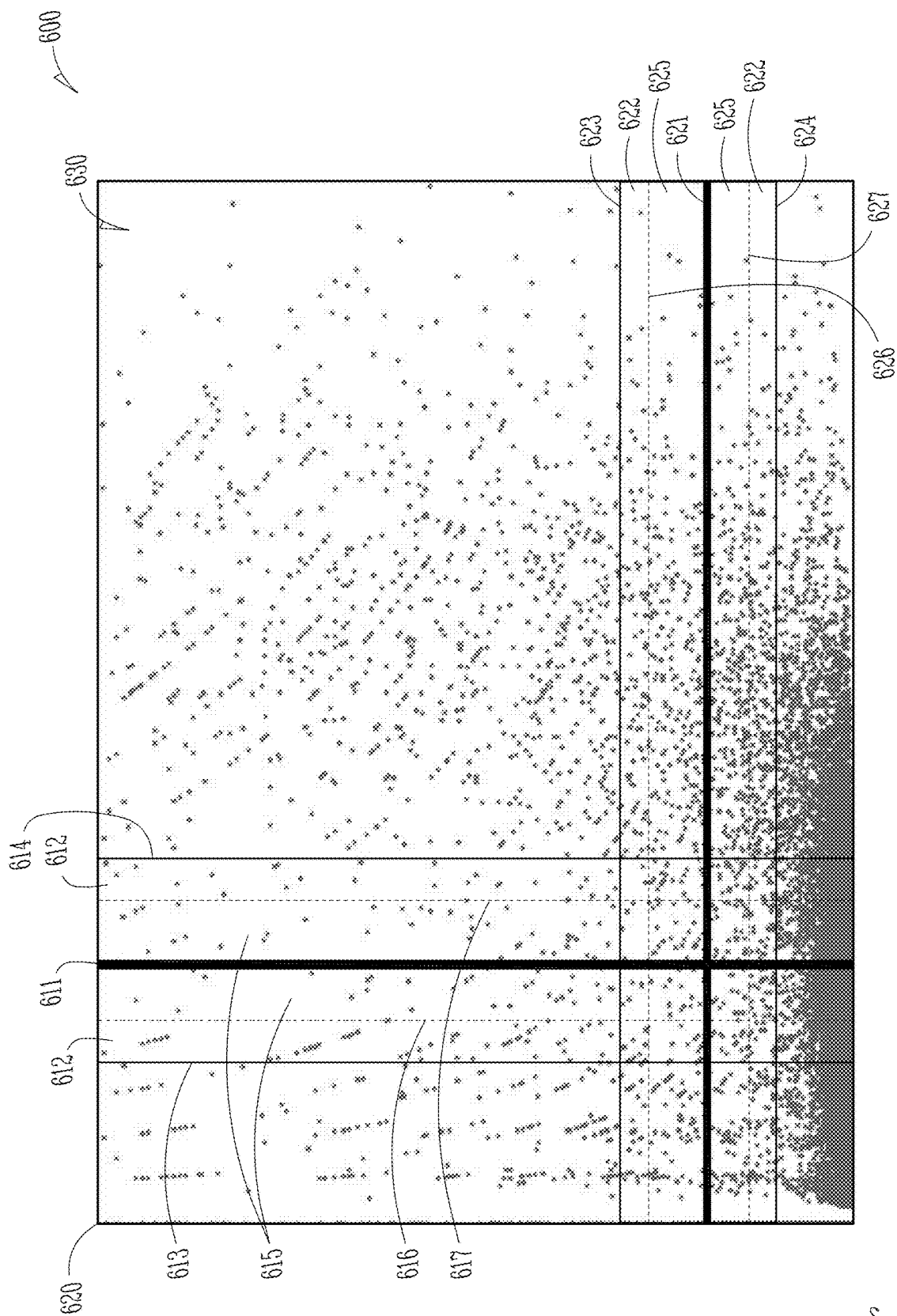
FIG. 6 illustrates an example cardiac event graph including heart information data, thresholds, safety zones, and target zones.

FIG. 6 illustrates an example cardiac event graph 600 including heart information data 630, an x-axis 610, a y-axis 620, first and second thresholds 611 and 621, safety zones 612 and 622, target zones 615 and 625, upper boundaries 616 and 626, and lower boundaries 617 and 627. The heart information data 630 is taken from a set of physiological information of a patient. The heart information data 630 shown is represented by small dots and plotted on the graph based upon two different parameters, one parameter corresponding to the x-axis 610 and the other parameter corresponding to the y-axis 620. In an example, the x-axis 610 parameter is a heart rate (HR) scatter ratio and the y-axis 620 parameter is a HR double-decrement ratio. In other examples, the x-axis 610 and y-axis can represent other representations of one or more other physiologic parameters, or combinations of one or more other physiologic parameters of interest in arrhythmia detection.

Threshold 611, safety zone 612, lower safety boundary 613, upper safety boundary 614, target zone 615, lower boundary 616, and upper boundary 617 correspond to the x-axis 610 and the data type the x-axis 610 represents. The threshold 611 corresponds to the heart data type of the 610. The target zone 615 is defined by the lower boundary 616 below the threshold 611 and the upper boundary 617 above the threshold. The arrhythmia circuit can detect candidate cardiac events within the target zone 615. The arrhythmia circuit can adjust the threshold 611, the lower boundary 616, the upper boundary 617, or any combination thereof in response to received user information about the candidate cardiac event. The safety zone 612, defined by the lower safety boundary 613 and the upper safety boundary 614, can represent the area in which adjustments can be made. Adjustments of the threshold 611, the lower boundary 616, and the upper boundary 617 can be restricted to within the safety zone 612.

Threshold 621, safety zone 622, lower safety boundary 623, upper safety boundary 624, target zone 625, lower boundary 626, and upper boundary 627 correspond to the y-axis 620 and the data type the y-axis 620 represents. The threshold 621 corresponds to the heart data type of the 620. The target zone 625 is defined by the lower boundary 626 below the threshold 621 and the upper boundary 627 above the threshold. The arrhythmia circuit can detect candidate cardiac events within the target zone 625. The arrhythmia circuit can adjust the threshold 621, the lower boundary 626, the upper boundary 627, or any combination thereof in response to received user information about the candidate cardiac event. The safety zone 622, defined by the lower safety boundary 623 and the upper safety boundary 624, can represent the area in which adjustments can be made. Adjustments of the threshold 621, the lower boundary 626, and the upper boundary 627 can be restricted to within the safety zone 622.

Figure 7:
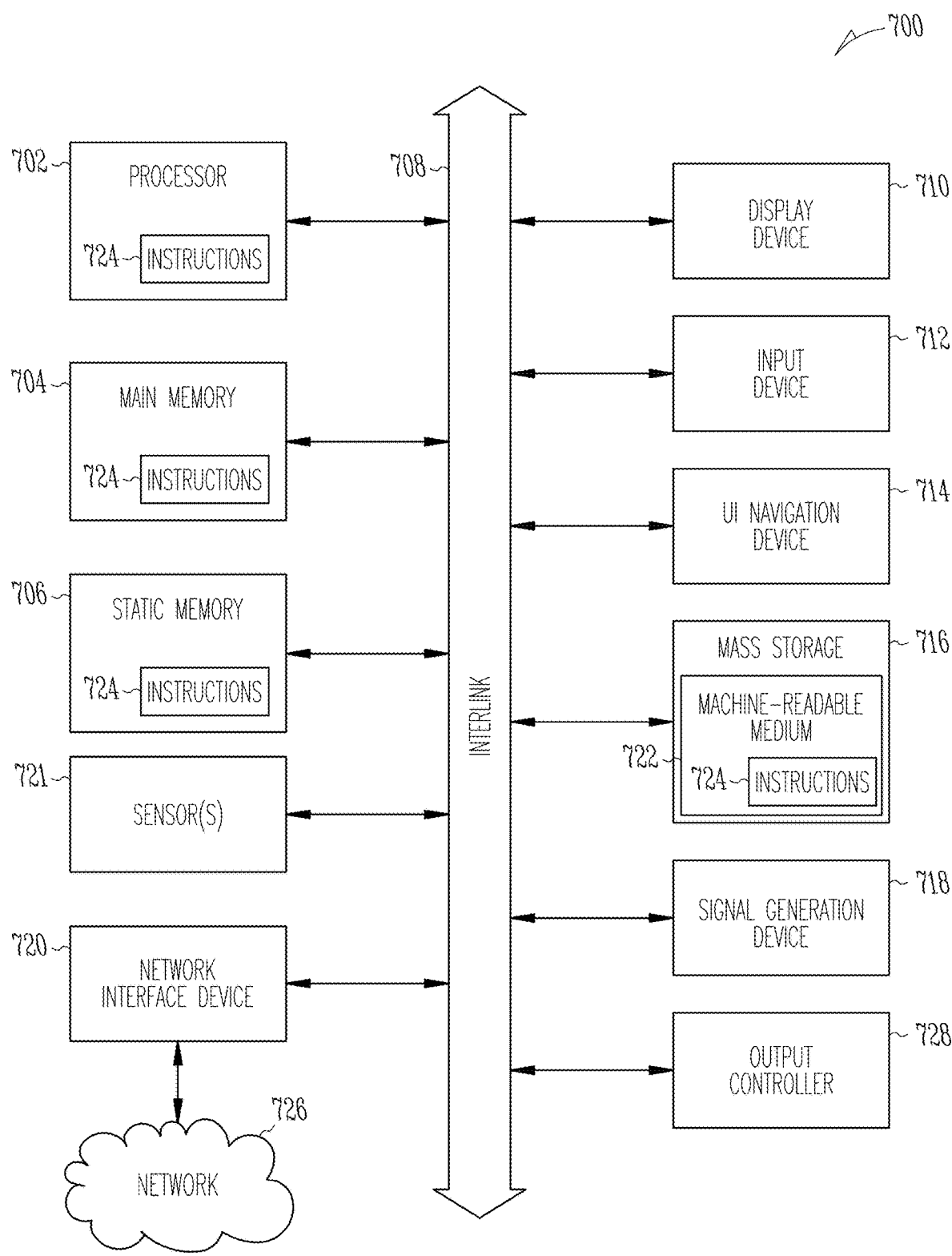
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of various portions of the LCP device, the 1 MB, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments. By way of examples and not limitation, one or more features of the stochastic modulator illustrated in FIG. 9 may be incorporated into other stochastic modulators, and one or more features of the user interface illustrated in FIG. 11 may be incorporated into the systems illustrated in other figures.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device learning system comprising:
   an input circuit configured to receive physiological information of a patient;
   an arrhythmia circuit configured to detect a candidate cardiac event about a threshold using the received physiological information of the patient; and
   a user interface configured to display the candidate cardiac event to a user, and to receive user information about whether the candidate cardiac event should be above or below the threshold,
   wherein the arrhythmia circuit is configured to adjust an arrhythmia detection threshold using the received user information that the candidate cardiac event should be above or below the threshold.

2. The system of claim 1, wherein the arrhythmia circuit is configured to detect the candidate cardiac event using a detection parameter, and
   wherein the arrhythmia circuit is configured to adjust at least one of the threshold or the detection parameter using the received user information that the candidate cardiac event should be above or below the threshold.

3. The system of claim 2, including:
   a counter,
   wherein the arrhythmia circuit is configured to adjust a count of the counter in response to the received user information that the candidate cardiac event should be above or below the threshold, and
   wherein the arrhythmia circuit is configured to adjust at least one of the threshold or the detection parameter when the count exceeds an update threshold.

4. The system of claim 2, wherein the arrhythmia circuit is configured to detect a cardiac arrhythmia using the adjusted threshold or the adjusted detection parameter.

5. The system of claim 1, wherein the arrhythmia circuit is configured to adjust the threshold within a predefined safety zone using the received user information.

6. The system of claim 5, wherein the arrhythmia circuit is configured to detect a cardiac arrhythmia using the adjusted threshold.

7. The system of claim 1, wherein the received user information about whether the candidate cardiac event should be above or below the threshold includes positive received user information, neutral received user information, or negative received user information.

8. The system of claim 1, wherein the arrhythmia circuit is configured to adjust a confidence parameter in response to the received user information that the candidate cardiac event should be above or below the threshold.

9. The system of claim 1, wherein the arrhythmia circuit is configured to detect the candidate cardiac event within a target zone about the threshold, and
   wherein the target zone includes a lower boundary below the threshold, and an upper boundary above the threshold.

10. The system of claim 9, wherein the threshold is centered between the upper boundary and the lower boundary.

11. The system of claim 9, wherein the upper boundary is a predefined amount above the threshold and the lower boundary is a predefined amount below the threshold.

12. The system of claim 9, wherein the upper boundary is a selectable amount above the threshold and the lower boundary is a selectable amount below the threshold.

13. A medical device learning method comprising:
    receiving physiological information of a patient using an input circuit;
    detecting, using an arrhythmia circuit, a candidate cardiac event about a threshold using the physiological information of the patient;
    displaying, using a user interface, the candidate cardiac event to a user;
    receiving, using the user interface, user information about whether the candidate cardiac event should be above or below the threshold; and
    adjusting, using the arrhythmia circuit, an arrhythmia detection threshold using the received user information that the candidate cardiac event should be above or below the threshold.

14. The method of claim 13, wherein detecting the candidate cardiac event includes using a detection parameter, and
    wherein adjusting the arrhythmia detection threshold includes adjusting at least one of the threshold or the detection parameter using the received user information that the candidate cardiac event should be above or below the threshold.

15. The method of claim 14, including detecting, using the arrhythmia circuit, a cardiac arrhythmia using the adjusted threshold or the adjusted detection parameter.

16. The method of claim 13, wherein adjusting the arrhythmia detection threshold includes adjusting the threshold within a predefined safety zone using the received user information that the candidate cardiac event should be above or below the threshold.

17. The method of claim 13, including:
    detecting, using the arrhythmia circuit, the candidate cardiac event within a target zone about the threshold,
    wherein the target zone includes a lower boundary below the threshold, and an upper boundary above the threshold.

18. The method of claim 13, wherein the received user information about whether the candidate cardiac event should be above or below the threshold includes positive received user information, neutral received user information, or negative received user information.

19. The method of claim 13, including:
- adjusting a count of a counter, using the arrhythmia circuit, in response to the received user information that the candidate cardiac event should be above or below the threshold; and
- adjusting, using the arrhythmia circuit, at least one of the threshold or the detection parameter when the count exceeds an update threshold.

20. The method of claim 13, including adjusting a confidence parameter in response to the received user information that the candidate cardiac event should be above or below the threshold using the arrhythmia circuit.

* * * * *